United States Patent
Fuhr et al.

(10) Patent No.: US 8,789,495 B2
(45) Date of Patent: Jul. 29, 2014

(54) METHOD AND APPARATUS FOR CONSERVING DEEP-SEA ORGANISMS

(75) Inventors: Guenter R. Fuhr, Berlin (DE); Heiko Zimmermann, St. Ingbert (DE); Charli Kruse, Herrnburg (DE); Robert Lemor, Saarbruecken (DE)

(73) Assignee: Fraunhofer-Gesellschaft zur Foerderung der Angewandten Forschung e.V., Munich (DE)

( * ) Notice: Subject to any disclaimer, the term of this patent is extended or adjusted under 35 U.S.C. 154(b) by 300 days.

(21) Appl. No.: 13/319,182

(22) PCT Filed: Jun. 14, 2010

(86) PCT No.: PCT/EP2010/003558
§ 371 (c)(1),
(2), (4) Date: Nov. 7, 2011

(87) PCT Pub. No.: WO2010/145791
PCT Pub. Date: Dec. 23, 2010

(65) Prior Publication Data
US 2012/0079990 A1  Apr. 5, 2012

(30) Foreign Application Priority Data
Jun. 17, 2009 (DE) .................. 10 2009 025 268

(51) Int. Cl.
*A01K 63/02* (2006.01)
(52) U.S. Cl.
CPC ...................................... *A01K 63/02* (2013.01)
USPC .......................................... 119/201; 119/203
(58) Field of Classification Search
CPC .................................................... A01K 63/02
USPC ................................................... 119/201, 203
See application file for complete search history.

(56) References Cited

U.S. PATENT DOCUMENTS

| | | | | |
|---|---|---|---|---|
| 3,367,061 | A | * | 2/1968 | Primmer et al. ................... 43/55 |
| 3,735,737 | A | * | 5/1973 | Budge ........................... 119/201 |
| 4,416,118 | A | | 11/1983 | Brister |
| 5,310,427 | A | * | 5/1994 | Manome ....................... 119/201 |

(Continued)

FOREIGN PATENT DOCUMENTS

| | | | | | |
|---|---|---|---|---|---|
| JP | 03210135 | A | * | 9/1991 | ............. A01K 63/02 |
| JP | 04287629 | A | * | 10/1992 | ............. A01K 63/02 |
| JP | 2004166575 | A | | 6/2004 | |
| WO | 2007060608 | A2 | | 5/2007 | |

OTHER PUBLICATIONS

Koyama, "Cell biology of deep-sea multicellular organisms", Cytotechnology, vol. 55, pp. 125-133 (2007).

(Continued)

*Primary Examiner* — Kristen C Hayes
(74) *Attorney, Agent, or Firm* — Caesar, Rivise, Bernstein, Cohen & Pokotilow, Ltd.

(57) ABSTRACT

The invention relates to a method for conserving at least one biological deep-sea organism (1) comprising the steps of collecting the biological organism (1) in a deep-sea trapping device (110); cooling the biological organism (1) with a cooling device (120), wherein the biological organism (1) is put in a frozen condition; and moving the frozen biological organism (1), preferably with the trapping device (110), to a normal-pressure environment. The invention further relates to a conservation apparatus (100) for conserving at least one biological deep-sea organism (1).

13 Claims, 7 Drawing Sheets

(56) References Cited

U.S. PATENT DOCUMENTS

| 8,553,501 | B1* | 10/2013 | Cota | 367/131 |
|---|---|---|---|---|
| 2002/0088482 | A1 | 7/2002 | Courson et al. | |
| 2007/0087321 | A1 | 4/2007 | Pribenszky et al. | |
| 2007/0245971 | A1* | 10/2007 | Rayner | 119/201 |
| 2012/0103271 | A1* | 5/2012 | Kong | 119/203 |
| 2013/0219769 | A1* | 8/2013 | Hey et al. | 43/4.5 |

OTHER PUBLICATIONS

Koyama et al., "Pressure-stat aquarium system designed for capturing and maintaining deep-sea organisms", Deep-Sea Research I, vol. 49, pp. 2095-2102 (2002).

Lever, "Life fish caught at record depth", http://news.bbc.co.uk/2/hi/science/nature/7525552.stm (Jul. 31, 2008).

Pradillon et al., "Pressure Vessels for In Vivo Studies of Deep-Sea Fauna", High Pressure Research, vol. 24, No. 2, pp. 237-246 (2004).

Shillito et al., "Live capture of megafauna from 2300 m depth, using a newly designed Pressurized Recovery Device", Deep-Sea Research I, vol. 55, pp. 881-889 (2008).

Yayanos, "Recovery and Maintenance of Live Amphipods at a Pressure of 580 Bars from an Ocean Depth of 5700 Meters", Science, vol. 200, pp. 1056-1059 (1978).

International Search Report for PCT/EP2010/003558 dated Jul. 18, 2011.

* cited by examiner

METHOD AND APPARATUS FOR CONSERVING DEEP-SEA ORGANISMS

BACKGROUND OF THE INVENTION

The invention relates to a method for conserving (or: preserving) biological material in the deep sea, in particular to a method for capturing or collecting at least one biological organism in the deep sea and transferring it to surroundings under normal pressure. Moreover the invention relates to a conservation apparatus which is designed for conserving biological material in the deep sea. Applications of the invention are the retrieval and culturing of biological material from the deep sea.

Various methods are known for characterizing biological material. While genomic analysis may be carried out on dead biological material, biochemical analyses at a molecular, cellular or physiological level require the presence of viable cells in the living organism or in an in vitro culture. An in vitro culture in particular makes it easier to carry out laboratory methods and to use instruments for characterizing the biological material and to make biotechnological or pharmacological use of the biological material. While standard methods are known for the in vitro culturing of cells from most organisms living on the earth's surface at normal pressure, considerable limitations apply to the investigation of biological material whose natural habitat is the deep sea (depth below 2000 m, for example below 2300 m or 4000 m, abyssal, in particular below 5000 m to 11000 m, hadal).

Biological cells from deep-sea macrofauna organisms have hitherto only been successfully isolated and cultured down to a depth of around 1200 m (see S. Koyama in "Kryotechnology", volume 55, 2007, pp. 125-133). These methods are, however, restricted to organisms which can tolerate a pressure drop in the hydrostatic pressure of their habitat down to normal pressure (atmospheric pressure), i.e. which are not obligate barophiles, such as for example the deep-sea eel. The methods described by S. Koyama are, however, not applicable to the majority of deep-sea organisms, because they live at considerably greater depth, in particular below 3000 m and are typically not barophilic. Biological organisms from the deep sea are therefore not yet represented in laboratory cell cultures, or accessible for investigations at the earth's surface. Attempts have also been made to retrieve living organisms from great depths and to keep them alive in the laboratory and at the surface in pressurized aquariums or by adaptation to normal pressure. Such attempts have, however, only met with success down to a depth of 2300 m (see B. Shillito et al. In "Deep-Sea Research I" volume 55, 2008, pp. 881-889).

In practice, the reasons behind the so far unsuccessful attempts to retrieve living cell material and to establish viable in vitro cell cultures which are stable over the long term are considered to be that, with increasing depth, organisms become increasingly adapted to high pressures and to high pressure constancy in their natural habitat, and in the deep sea an adaptation to a constantly low or, near hot springs, high temperature and a low tolerance to temperature changes have developed, and that, at great depths, in particular deeper than 5000 m, the organisms are generally barophilic. It may furthermore be assumed that the macromolecules involved in cellular biological processes are optimized for high pressures (up to 110 MPa at a depth of 11,000 m) and reduce or completely lose their function at lower pressures.

Capture gear for collecting biological organisms in the deep sea and transferring them to the surface while maintaining cell vitality is not yet available. Furthermore, the technical limitations involved in handling living organisms, such as in animal keeping, cell culturing or isolation methods, under high pressures have not yet been overcome. Another problem which arises here is the considerable time pressure which occurs when transporting organisms from the deep sea to the earth's surface. Because of these limitations, only little information is so far available about which biological cells may be cultured, isolated and/or multiplied from what kinds of tissue.

The objective of the invention is to provide an improved method for conserving biological material from the deep sea, with which the disadvantages and limitations of conventional techniques may be overcome and which in particular makes it possible to retrieve at least one biological organism from the deep sea while maintaining the viability of its cells and to transfer the cells into a stable in vitro culture capable of multiplication. It is furthermore an objective of the invention to provide an improved conservation apparatus, with which the disadvantages and limitations of conventional techniques may be overcome and which has an extended range of applications in collecting biological organisms in the deep sea.

These objectives are achieved by a conservation method and a conservation apparatus of the invention.

SUMMARY OF THE INVENTION

According to a first aspect of the invention, the above objective is achieved by a conservation method (preservation method) in which at least one biological organism is frozen in the deep sea and, in the frozen state, is transferred into surroundings under normal pressure. The method according to the invention comprises a first step, in which the at least one biological organism is captured with a trapping device. The biological organism is positioned with the trapping device in its natural surroundings, i.e. in seawater, immediately adjoining a cooling device. In a second step, the method according to the invention comprises cooling the biological organism with the cooling device until the biological organism exhibits a temperature below its freezing point. In the frozen state, the biological organism is a solid, the form (shape, size) of which is advantageously independent of the external pressure. In the frozen state, the biological organism may thus be transferred in a third step into an environment at atmospheric pressure, i.e. to the surface of the ocean. A sample may in particular be stored in the frozen state, so eliminating the time pressure until cell isolation which arises in conventional methods.

According to a second aspect of the invention, the above objective is achieved by a conservation apparatus (preservation apparatus) which is designed for conserving at least one biological organism in the deep sea, and comprises a trapping device and a cooling device. The trapping device of the conservation apparatus according to the invention is configured to accommodate the biological organism in the deep sea, i.e. to position it in a cooling zone of the cooling device. The cooling device is designed to cool the biological organism from a temperature in its natural habitat to a temperature below its freezing point. The cooling device is characterized by active cooling of the biological organism with a cooling medium. The conservation apparatus according to the invention is advantageously an autonomous device which is mobile undersea and is adapted for transport from the deep sea to the surface of the ocean. Using the conservation apparatus, the frozen biological organism may be transferred pressure-free in the solid state into surroundings under normal pressure, in order to be subjected there to further steps, in particular for conservation, investigation and/or culturing.

The "biological organism" generally includes any living structure comprising at least one biological cell, in particular microbial or animal cells of lower or higher organisms. Using the method according to the invention, individuals from all strains occurring in the deep sea, including fish, crabs or unicellular organisms, such as foraminifera, may advantageously be collected, frozen and retrieved from the deep sea. The organisms living in the deep sea may be sediment-dwelling or floating.

The trapping device used according to the invention may generally be of a structure and form which is suitable for localizing the biological organism in the cooling zone of the cooling device. According to a preferred embodiment of the invention, the trapping device provides an enclosed space for accommodating the at least one biological organism. The trapping device is preferably equipped with at least one thermally insulated chamber. Preferably, the whole biological organism together with the surrounding seawater is frozen in the chamber. This advantageously allows conservation in a state with no mechanical damage to the biological organism. Alternatively, conservation may be provided in the chamber in a state in which the organism is broken up into parts, for example tissue fragments.

Advantageously, no particular requirements apply with regard to the mechanical stability of the chamber. In the deep sea, the chamber is filled with seawater with a balanced internal and external pressure. On transfer to shallower depths or to the surface of the ocean, on the other hand, the interior of the chamber is entirely filled with a solid consisting of the sea water and at least one biological organism, such that no internal pressure, which could jeopardize the stability of the chamber, arises even under reduced external pressure. According to a preferred feature of the invention, the chamber of the trapping device is therefore constructed without or with reduced pressure resistance against the hydrostatic pressure which prevails in the deep sea.

According to further advantageous embodiments of the invention, collecting at least one biological organism into the trapping device involves luring, actively flushing in (e.g. aspirating) or a combination of luring and flushing in. To this end, the trapping device is preferably equipped with a collecting device which comprises at least one of a lure device and a flushing device. The biological organism is preferably lured by generating a light stimulus and/or a chemical stimulus. The light stimulus may be a light source provided in the chamber of the trapping device, such as for example an active light source or a luminescent zone in the chamber. To form the chemical stimulus, the trapping device may be equipped with a substance source, which simulates the presence of nutrients or other stimuli.

If, according to another embodiment of the invention, the conservation device is equipped with a sensor device with which collecting of at least one biological organism in the trapping device is detectable, it is possible to simplify control of the conservation apparatus, particularly turning on of the cooling. The sensor device for example comprises a light sensor or a camera. The light sensor may advantageously detect the presence of the biological organism by a simple scattered light measurement in the chamber. The camera allows an image of the interior of the chamber to be taken. Advantageously, in addition to detecting the biological organism, monitoring and control functions of the conservation apparatus may be carried out therewith. Alternatively or in addition, the biological organism may be detected electrically, for example by an impedance measurement in the chamber.

There are advantageously various options for carrying out cooling and freezing of the at least one biological organism in the deep sea. According to a first variant, a fluid cooling medium may be introduced into a cooling line, which is arranged in an internal wall of the trapping device, in particular an internal wall of the chamber. The seawater and the at least one biological organism in the trapping device are advantageously brought into direct thermal contact with the cooling line. Elevated cooling efficiency may thus be achieved. Prior to introduction of the coolant, the cooling line is preferably filled with a fluid filling medium. The filling medium ensures pressure equalization before the start of cooling. On introduction of the cooling medium, the filling medium may be displaced from the cooling line and for example released into the surroundings of the conservation apparatus. According to a second variant, cooling of an internal wall of the trapping device, in particular of an internal wall of the chamber, may be provided by at least one thermal bridge being formed between the cooling medium in a coolant tank and the internal wall. The thermal bridge is a component which has thermal conductivity which is high in comparison with the thermally insulated outer wall of the trapping device. Cooling via at least one thermal bridge advantageously enables simplified construction of the conservation apparatus according to the invention.

The cooling medium used according to the invention is generally a solid or flowable (fluid, in particular liquid or gaseous) substance which is selected as a function of temperature, volume and heat capacity such that, on heat exchange with the interior of the trapping device, the latter may be completely frozen. The cooling medium comprises, for example, solid carbon dioxide or liquid nitrogen or liquid nitrogen vapor. According to another variant, the cooling medium may be a solid, such as a metal or ceramic block for example, which has been supercooled for example to −196° C. The solid may comprise cavities, for example being porous, and contain fluid coolant. A solid cooling medium may furthermore comprise frozen water, in particular salt water or fresh water. In this case, the cooling medium advantageously forms a buoyancy element which may contribute to the movement of the conservation apparatus.

The coolant is preferably arranged in a thermally insulated coolant tank. The coolant may be kept stable in the coolant tank over a sufficiently long period which may, for example, amount to at least 6 hours, preferably at least 10 hours, for example 24 hours or more, even 2 or more days, for example 10 days or more without the trapping device being cooled. One particularly preferred embodiment of the invention provides that cooling is not actuated until a predetermined time in order to freeze the interior of the trapping device. The start of cooling is selected such that freezing does not occur until a biological organism, optionally an organism of a desired biological species, is present in the trapping device.

Cooling is preferably switched on by opening at least one valve in at least one feed line from the coolant tank to the cooling line. In the event of cooling by means of at least one thermal bridge, the thermal bridge is preferably activated, for example by mechanical switching, in order to create the thermal coupling between the coolant in the coolant tank and the internal wall of the trapping device. Cooling is particularly preferably switched as a function of a signal from the sensor device with which collecting of the biological organism in the trapping device is indicated.

The conservation apparatus according to the invention may advantageously be designed to ascend from the deep sea to the surface of the ocean without an active mechanical drive. The ascent may be effected exclusively by buoyancy. To this end, the conservation apparatus is equipped with a buoyancy device, which may preferably be switched on and off in order to control the position (depth) and/or ascent of the conservation apparatus. If the coolant comprises a deep frozen block of ice, this may contribute to buoyancy. In this case, for surfacing a ballast mass optionally provided on the conservation apparatus is separated from the conservation apparatus.

A variant of the invention in which the buoyancy device is actuated by conversion of cooling medium into a gaseous state is particularly preferred. The conservation apparatus may be equipped with a buoyancy vessel into which the gaseous cooling medium is introduced. The buoyancy vessel preferably comprises a resilient vessel wall, such that it may be unfolded on introduction of the gaseous cooling medium. Thermodynamic simulations have shown that a buoyancy vessel can unfold even under the elevated hydrostatic pressure in the deep sea. Depending on the specific pressure conditions, in particular depth, at which the biological organism is frozen, it may be provided that the buoyancy vessel is used immediately upon freezing or optionally only once it reaches a shallower depth, i.e. at a lower pressure, for example from 1000 m upwards.

Activating buoyancy by introducing gaseous cooling medium into the buoyancy vessel has the particular advantage that the method according to the invention may be completely automated. The conservation apparatus with the filled coolant tank may be lowered into the deep sea and remain there until, possibly under the effect of luring or active flushing in, the at least one biological organism is caught. As soon as the sensor device detects that the biological organism has been collected, cooling is switched on such that the biological organism is frozen. At the same time, the buoyancy vessel filled with the spent coolant is unfolded until buoyancy is sufficiently high for the conservation apparatus to ascend. As a result, the conservation apparatus surfaces automatically with the frozen contents of the trapping device.

Freezing in the deep sea may advantageously proceed as is known per se from conventional cryoconservation. For example, a cryoprotectant, which ensures gentle freezing of the at least one biological organism and/or influences crystal formation during freezing, may be added to the interior of the trapping device, in particular once the least one biological organism has been collected. Alternatively or in addition, mechanical preparation of the at least one biological organism may be provided, in which, prior to freezing in the trapping device, the least one biological organism is broken up into tissue fragments.

Advantageously, various options are available for the further processing or treatment of the frozen sample after it has been transferred to surroundings under normal pressure. Preferably, cooling is maintained in the surroundings under normal pressure (atmospheric surroundings). The sample is left in the frozen state after surfacing. In this state, the sample is advantageously mechanically stable, such that the biological cells or at least the components thereof are obtained in a state in which they are potentially viable or cell-biologically functional.

The biological organism may then be broken up in the frozen state under normal pressure. Breaking up may be performed mechanically in order to separate frozen seawater from the biological organism and/or to break the biological organism up into pieces, for example tissue fragments.

The latter is advantageous if the following steps are limited to culturing certain cell types from the biological organism.

According to a further variant of the method according to the invention, the biological organism or parts thereof may be thawed. Depending on the desired subsequent use of the biological cells, thawing may be carried out under normal pressure or under elevated pressure in a pressure chamber. The cells obtained on thawing are then preferably cultured, wherein, depending on their suitability for culturing, they may be cultured under normal pressure or under elevated pressure using per se known culture methods.

The use of cryoconservation for the retrieval of biological organisms in the deep sea constitutes an independent subject matter of the invention.

BRIEF DESCRIPTION OF THE DRAWINGS

Further details and advantages of the invention will be described below with reference to the attached drawings. The figures show as follows:

FIGS. 9A to 9G: show a schematic illustration of a preferred embodiment of the conservation method according to the invention;

FIGS. 11A to 11D: show a schematic illustration of culturing steps provided according to the invention.

DETAILED DESCRIPTION OF PREFEREED EMBODIMENTS

Embodiments of the conservation apparatus according to the invention are illustrated schematically in the drawings to show the components of the conservation apparatus. It is emphasized that these representations are not to scale. The proportions, in particular of the cooling device relative to the trapping device, may differ significantly from the illustrations (see for example FIG. 4).

Figure 1:
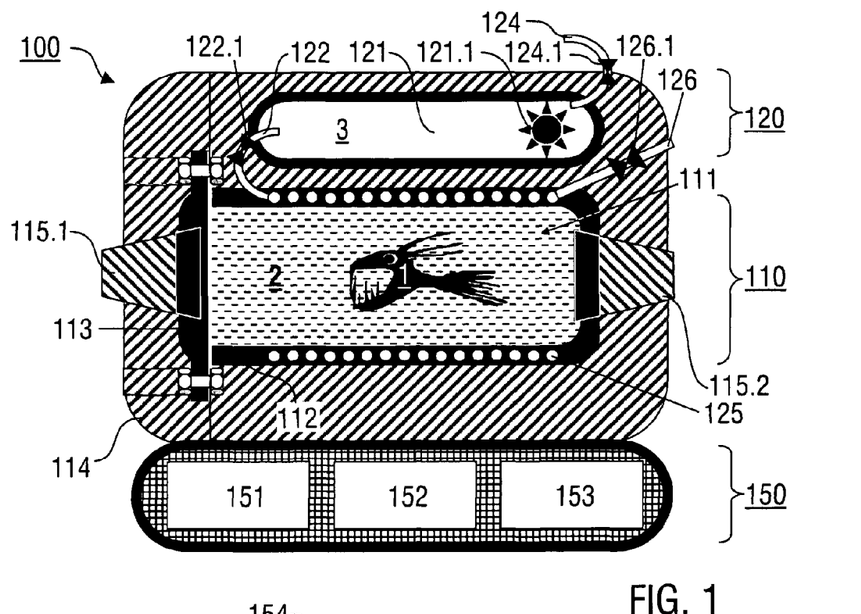
FIGS. 1 to 8: show schematic sectional views of various embodiments of the conservation apparatus according to the invention.

FIG. 1 shows a schematic sectional view of a first embodiment of the conservation apparatus 100 according to the invention. The conservation apparatus 100 comprises the trapping device 110, the cooling device 120 and the control device 150. Further components, such as for example a sensor device, a preparation device and/or a buoyancy device, which are described below with reference to FIGS. 2 to 8, may optionally be provided. FIG. 1 shows the conservation apparatus 100 by way of example in a state in which an organism 1 with surrounding seawater 2 is positioned and frozen in the trapping device 110.

The trapping device 110 comprises a chamber 111, which is formed by an internal wall 112 and a front wall 113 and is for example of a cylindrical shape. The conservation apparatus 100 may alternatively be equipped with a plurality of chambers which may be frozen jointly or selectively. The internal diameter of the chamber 111 is for example selected in the range from 1 cm to 100 cm, while the axial length of the chamber 111 is selected in the range from 5 cm to 200 cm. The internal wall 112 and the front wall 113 are enclosed by a thermally insulating outer wall 114 which simultaneously provides thermal insulation for the cooling device 120. The cooling device 120 is completely surrounded by the thermally insulating outer wall 114. The internal wall 112 and the front wall 113 consist for example of metal, in particular stainless steel, or of a plastics material, in particular fiber-reinforced composite material, such as for example carbon or glass fiber reinforced composite material. If the chamber 111 is not pressure-resistant or exhibits reduced pressure resistance, the internal wall 112 and the front wall 113 may be constructed with a small thickness, for example in the range from 1 cm to 20 cm. The thickness of the outer wall 114, on the other hand, is selected in order to achieve sufficient thermal insulation. If the outer wall is for example formed from glass or ceramic beads in a foam composite material, the thickness preferably amounts to 10 cm to 50 cm.

The trapping device 110 moreover comprises two lids 115.1, 115.2, which are arranged at the axial ends of the chamber 111. The lids 115.1, 115.2 are conical components which seal the chamber 111 relative to its surroundings and may preferably be opened towards the interior of the chamber 111. Inward opening of the lids 115.1, 115.2 has the advantage that, as the external pressure drops when the conservation apparatus 100 comes to the surface, any residual internal pressure in the chamber 111 presses the lids 115.1, 115.2 firmly against the internal wall 112. The lids 115.1, 115.2 are, for example, thermally insulated with parts of the outer wall 114. The chamber 111 may additionally be opened by separating the front wall 113 from the internal wall 112. A screw fastening is provided to this end between the front wall 113 and the internal wall 112 (flanged joint). Alternatively, a single lid may be provided (see FIG. 4).

The cooling device 120 comprises a coolant tank 121 for accommodating the coolant 3, a feed line 122 with a feed valve 122.1 and a cooling line (hollow line) 125 which runs in the internal wall 112. In the embodiment of the invention shown in FIG. 1, an outlet line 126 with an outlet valve 126.1 is moreover provided, through which coolant may be released into the surroundings. The coolant tank 121 is filled before the conservation apparatus 100 is used, i.e. still under normal pressure, using a filling line 124 with a filling valve 124.1, which may be connected to a storage tank (not shown).

In the coolant tank 121 a delivery or pump device 121.1 is provided, which is shown schematically and with which the coolant 3 in the coolant tank 121 may be pressurized with a predetermined operating pressure. On actuation of the pump device 121.1 with the feed and outlet valves 122.1 open, the coolant is pumped through the cooling line 125 in order to cool the internal wall 112 of the chamber 111. The coolant 3 comprises for example liquid nitrogen. The volume of the coolant tank 121 is for example selected in the range from 1000 cm$^3$ to 1 m$^3$. By means of the coolant 3, the temperature of the internal wall 112 may be adjusted for example to the range from −60° C. to −196° C. The inventors have established that, at the elevated hydrostatic pressure prevailing in the deep sea, the typical coolants used for cryoconservation, such as in particular liquid nitrogen, are liquid in this temperature range.

The control device 150, which is shown schematically, comprises an energy supply 151, a control module 152 and a coupling device 153. The energy supply 151 contains for example electrical energy storage means such as accumulators or batteries. The energy supply 151 is connected to components 152, 153, the electrically actuatable valves 122.1, 126.1 and to the pump device 121.1. The control module 152 contains a circuit, with which various operating states of the conservation device 100, such as for example switching on of the cooling, opening or closing of the lids 115.1, 115.2 or actuation of a lure device (see below) may be controlled. The coupling device 153 is generally provided as a mechanical, hydraulic, electrical and/or data connection interface for connecting the conservation apparatus 100 to external equipment (not shown). The coupling device 153 also represents components (not shown in further detail), such as for example projections, sleeves, hooks and profiles, with which a connection cable may be connected for mechanically and/or electrically connecting the conservation apparatus 100 for example to a ship. The conservation apparatus 100 may, for example, also be optically connected with a ship via a light guide device. The light guide device may be provided for signal transfer and/or for guiding light for illumination or imaging purposes.

In order to carry out the method according to the invention, the conservation apparatus 100 is submerged in the ocean to the desired capture depth, which may for example be as deep as 11000 m. At least one lid 115.1, 115.2 is open in this state. The valves 122.1, 126.1 and 124.1 are closed. If it is detected that a biological organism 1, such as for example a deep-sea fish which is shown schematically, has been collected in the trapping device 110, the lids 115.1, 115.2 are closed. The feed valve 122.1 is then firstly opened. Due to the gas pressure which is exerted by the coolant in the coolant tank 121, the coolant is forced through the feed line 122 into the cooling line 125. Opening of the outlet valve 126.1 means that a filler, such as for example benzene, alcohol or low viscosity oil, previously present in the cooling line 125 and then the flowing coolant may pass into the surrounding seawater. In the process, the internal wall 112 and hence the seawater 2 containing the organism 1 present in the chamber 111 is cooled to freezing. The coolant flowing away into the external seawater is heated by heat exchange along the cooling line 125, emerging into the external seawater in the liquid or preferably gaseous state. Blocking of the mouth of the outlet line 126 by freezing water is avoided due to the natural movement and elevated heat capacity of the surrounding seawater.

In the frozen state, the entire system, apart from the volume of the coolant tank 121, the feed line 122 and the cooling line 125, is a solid and may therefore tolerate pressures up to an external pressure of more than 100 MPa. Pressure stability is achieved by appropriately thick walls only for the stated components and the control device 150. In the control device 150, pressure stability may be improved by packing any cavities which are present for example with a plastics material. In addition to cryoconservation in the deep sea, pressure stability is a substantial advantage of the conservation apparatus according to the invention because the structure and actuation of the conservation apparatus 100 may be simplified by this stability. The conservation apparatus 100 may additionally be equipped with buoyancy and/or ballast elements (not shown) which enable accelerated transfer to the depths of the sea or to the surface.

Once the contents of the chamber 111 have frozen, the conservation apparatus 100 may be transported into a zone with lower pressure, for example to a shallower depth or right up to the surface of the ocean. Transport proceeds for example using a carrier cable and/or a buoyancy device (see below). Since cooling is to be maintained at least for the duration of transport, the volume of the coolant tank 121 is selected to ensure that the cooling line 125 has a sufficient supply of coolant. The volume of the coolant tank 121 is typically 20 to 100 times greater than the volume of the chamber 111. These size ratios are not shown to scale in the figures.

Figure 2:
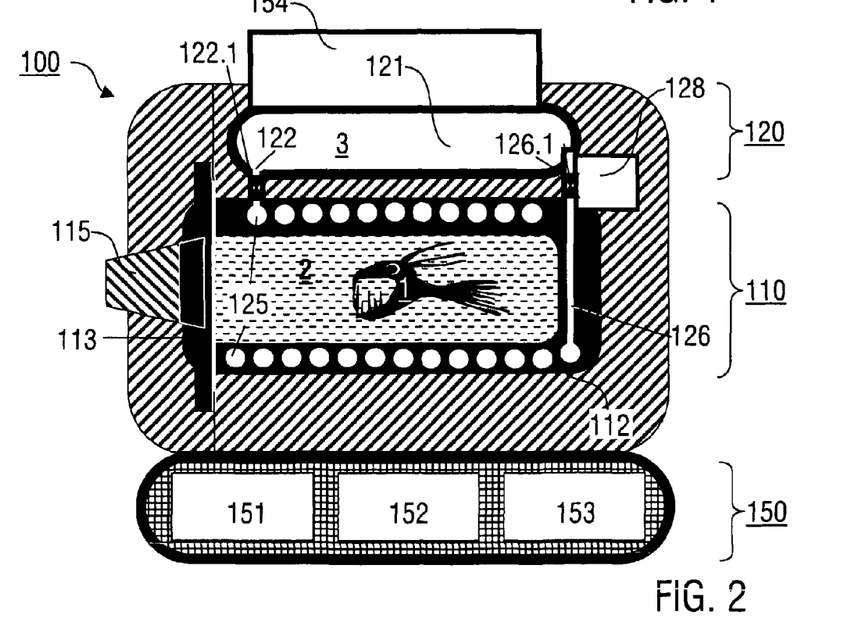
Figure 3:
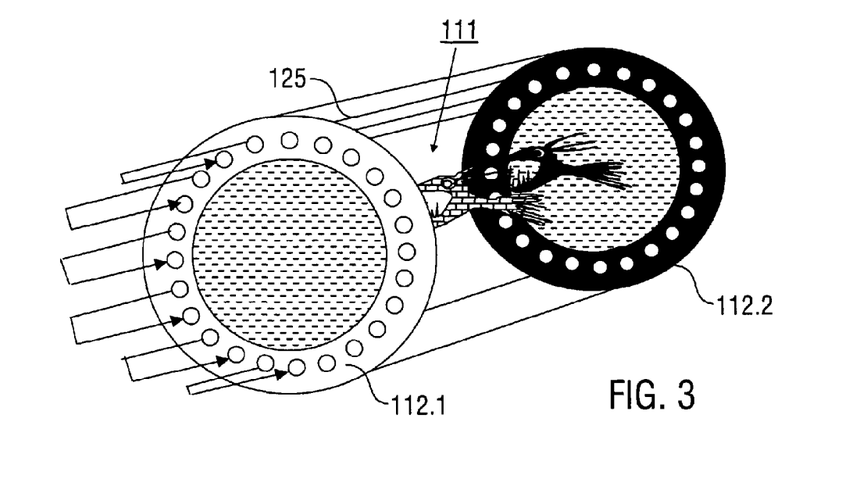

FIG. 2 shows a modified variant of the conservation apparatus 100 with the trapping device 110, the cooling device 120 and the control device 150. The conservation apparatus 100 is of similar construction to the embodiment according to FIG. 1. In contrast with the above-described embodiment, however, a coolant circuit is provided which runs from the coolant tank 121 via the feed line 122 with the feed valve 122.1 into the cooling line 125 and thence via the outlet line 126 with the outlet valve 126.1 back into the coolant tank 121 and/or a collecting tank 128 (shown schematically). FIG. 2 moreover shows that two lids are not necessary for functioning of the trapping device 110, a single lid 115 instead being sufficient. The latter is preferably integrated into the front wall 113. An optionally provided signaling device 154 is furthermore shown schematically, with which for example light or radio signals may be transmitted to the surface.

In the embodiment according to FIG. 2, the internal wall 112 of the trapping device is of pressure-resistant construction. To this end, the thickness of the internal wall 112 between the cooling line 125 and the outside of the internal wall 112 is at least 10 mm to 30 cm. Pressure stability is, however, not a mandatory feature. In this case too, prior to cooling, the cooling line 125 may be filled with a filler, such as for example benzene, alcohol or low viscosity oil, which is displaced by the incoming coolant, such as for example liquid nitrogen, at the start of cooling.

The arrangement of the cooling line 125 in the internal wall 112 may be optimized as is known per se from conventional heat exchangers. For example, the cooling line 125 may surround the chamber 111 in a spiral (FIGS. 1, 2) or be arranged in zig-zag manner extending in the lengthwise direction of the chamber 111, as shown schematically in the ghosted representation of FIG. 3. In this case, the cooling line of circular cross-section extends in the lengthwise direction of the chamber 111, the direction of flow of the coolant reversing (see arrows illustrating the cooling line 125) at the front end 112.1 and rear end 112.2 of the internal wall (not shown).

Figure 4:
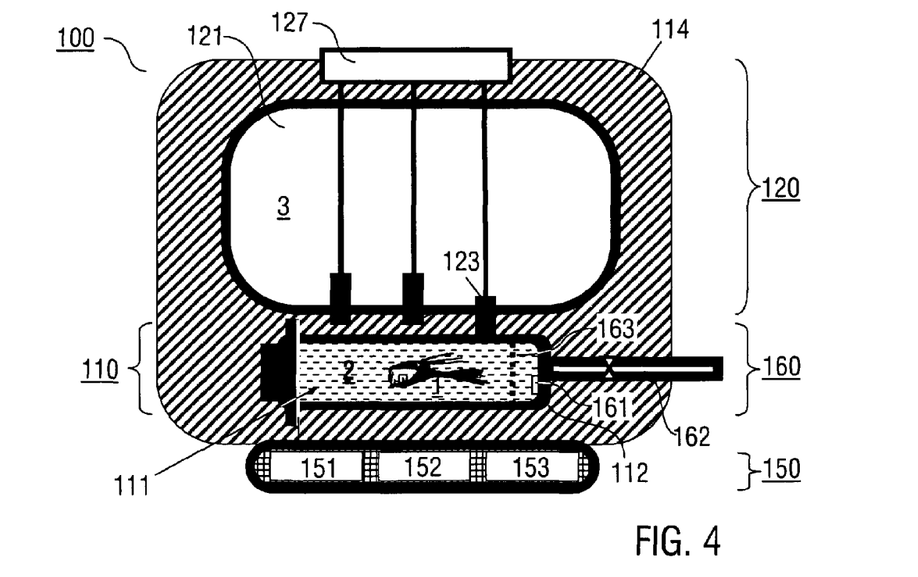

A further embodiment of the conservation apparatus 100 according to the invention with the trapping device 110, the cooling device 120 and the control device 150 is shown schematically in FIG. 4. In this embodiment, the chamber 111 is not cooled by a flowing coolant, but instead by thermal conduction via at least one thermal bridge 123. In this case, the cooling device 120 comprises the coolant tank 121, which is arranged in thermally insulated manner in the outer wall 114 of the trapping device 110. The cooling device 120 is furthermore equipped with a drive device 127 with which the thermal bridges 123 may be advanced from the coolant tank 121 through the outer wall 114 in order to be brought into thermal contact with the internal wall 112 of the chamber 111. FIG. 4 shows by way of example one thermal bridge 123 in the advanced position, while the remaining thermal bridges are still in the retracted state.

The embodiment according to FIG. 4 has the advantage that the internal wall 112 of the chamber 111 need not be pressure-resistant, since the internal pressure is always identical to the external pressure and, once the seawater 2 with the organism 1 has frozen, there is an incompressible solid present in the interior of the chamber 111. Only the coolant tank 121 with the drive device 127 need be made pressure-resistant.

FIG. 4 shows schematically a collecting device 160, which comprises a lure device 161 for luring the fish 1 into the trapping device 110 and/or a flushing device 162 for flushing (aspirating) the fish 1 into the trapping device 110. For luring, the lure device 161 may comprise a light source or luminescent dyes which are applied onto an inner side of the chamber 111. Deep-sea organisms advantageously frequently respond to such light signals. Light-emitting diodes, optical fibers etc. may alternatively be provided which optionally emit pulses of light and simulate the luminescent behavior of organisms in the deep sea. The flushing device 162 comprises a suction tube, which is connected to the chamber 111, and optionally a pump (not shown).

A screen or grating 163 may furthermore be arranged in the chamber 111 in order to retain and concentrate the organisms which have been flushed in. In this case, the addition of a cryoprotectant may advantageously be limited to the zone around the grating 163. In addition to the grating 163, a cutting tool may be arranged in the chamber 111, with which any flushed in organisms are broken down into tissue fragments under the action of the flow force in the chamber 111 and then retained on the grating 63.

Figure 5:
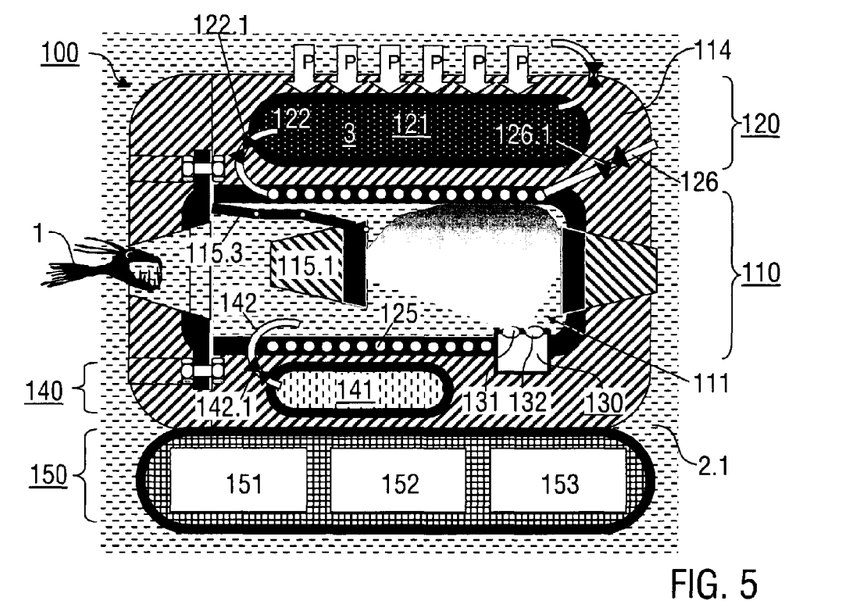
Figure 6:
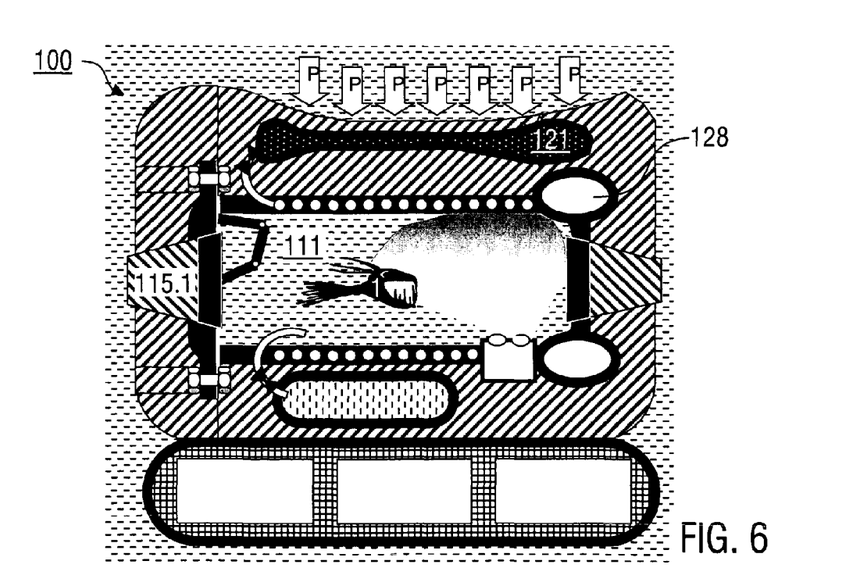

FIGS. 5 and 6 show an embodiment of the conservation apparatus 100 according to the invention in the seawater 2.1 shortly before capture of a deep-sea fish 1 (FIG. 5) and after freezing of the contents of the chamber 111 (FIG. 6). In this case the trapping device 110 and the cooling device 120 are constructed substantially as was described above with reference to FIG. 1. FIG. 6 additionally shows optionally provided pressure-resistant collecting tanks 128, into which the coolant can flow. Deviating from the above variant, however, no pump device is provided for conveying the coolant. Instead, the coolant tank 121 is constructed with reduced pressure stability. The pressure stability of the coolant tank 121 is selected such that, with valves 122.1, 126.1 closed, the coolant tank 121 filled with the cooling medium can withstand the external pressure in the deep sea. However, when the valves 122.1, 126.1 are opened at the start of cooling, in order to freeze the contents of the chamber 111 (FIG. 6), the internal pressure in the coolant tank 121 drops, such that the latter gradually collapses under the action of the external hydrostatic pressure. The coolant is here increasingly forced outwards through the cooling line 125 and the outlet line 126.

FIG. 5 furthermore schematically shows a lid lever 115.3, which is connected to the lid 115.1 and is provided to move it from the open state (FIG. 5) into the closed state (FIG. 6) or vice versa.

The lid lever 115.3 is equipped with an electrical drive motor (not shown) in a pressure-resistant chamber and/or a drive spring, which are electrically actuatable with the control module 152. FIG. 5 also shows a sensor device 130 which is arranged at least in part in the chamber 111 and comprises a light source 131 and an optical sensor, for example a camera 132 in a pressure-resistant housing. The sensor device 130 is connected to the control module 152. The sensor device 130 supplies a signal when collecting of the deep-sea fish 1 in the chamber 111 is detected. As a function of this signal, the lid 115.1 is closed with the control module 152 and cooling with the cooling device 120 is switched on. In addition to providing illumination for taking an image with the camera 132, the light source 131 may also be provided as a lure device. The deep-sea fish 1 is lured by the light source, which for example looks like a luminescent deep sea-organism.

FIG. 5 moreover shows a preparation device 140, which is designed to provide predetermined conservation conditions in the chamber 111, in particular for supplying a cryoprotectant. The preparation device 140 comprises a storage container 141, which is arranged in the outer wall 114 and is connected to the interior of the chamber 111 via a preparation line 142 having a preparation valve 142.1. The preparation device is actuated after closure of the lid 115.1 prior to or simultaneously with the cooling being switched on. By opening the preparation valve 142.1, the cryoprotectant, for example dimethyl sulfoxide, is passed into the chamber 111 by the pressure on the storage container 141. Alternatively or in addition, at least one cryoprotectant may be supplied by means of diffusion through a semipermeable area of the internal wall 112. According to a further modification of the conservation apparatus 100, a plurality of storage containers may be provided which for example introduce various cryoprotectants or other additives into the chamber 111. A storage container may also be used as a lure device for introducing a lure substance into the chamber 111.

Alternatively or in addition, the preparation device 140 may be designed for mechanical preparation of the organism 1. For example the preparation device 140 may comprise cutting tools which are designed to break up the organism 1 in the trapping device into individual tissue fragments. Moreover, the preparation device 140 may comprise injection tools, such as for example cannulas, needles or harpoons, which are designed for penetrating and optionally for injecting substances into the organism 1 in the trapping device. Advantageously, prior to freezing, the organism 1 may be broken down into small tissue fragments therewith or injected with cryoprotectants or also cryogenic media by the injection tools, which are abruptly thrust into the organism. In this way, tissue fragments comprising living cells are more readily obtained from cryoconservation. The cutting tools and/or injection tools may be integrated in mobile manner into the internal wall of the chamber 111 and actuated mechanically, for example with a pressure-resistant motor drive or a spring drive.

Figure 7:
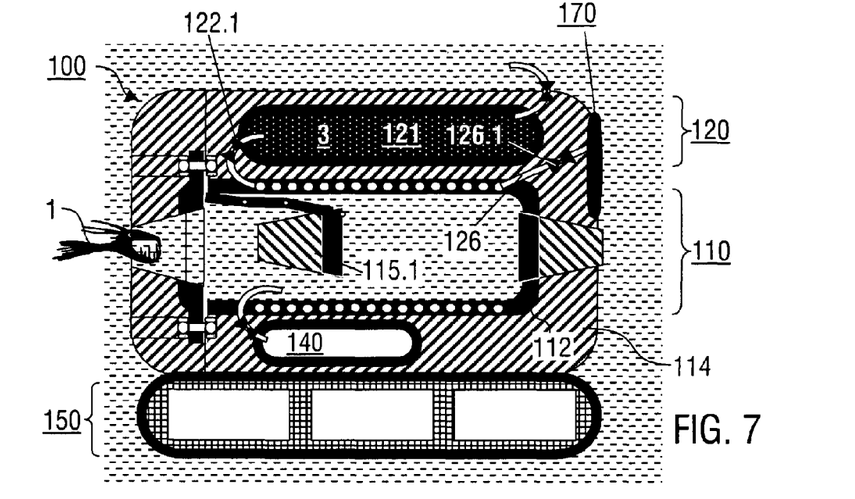
Figure 8:
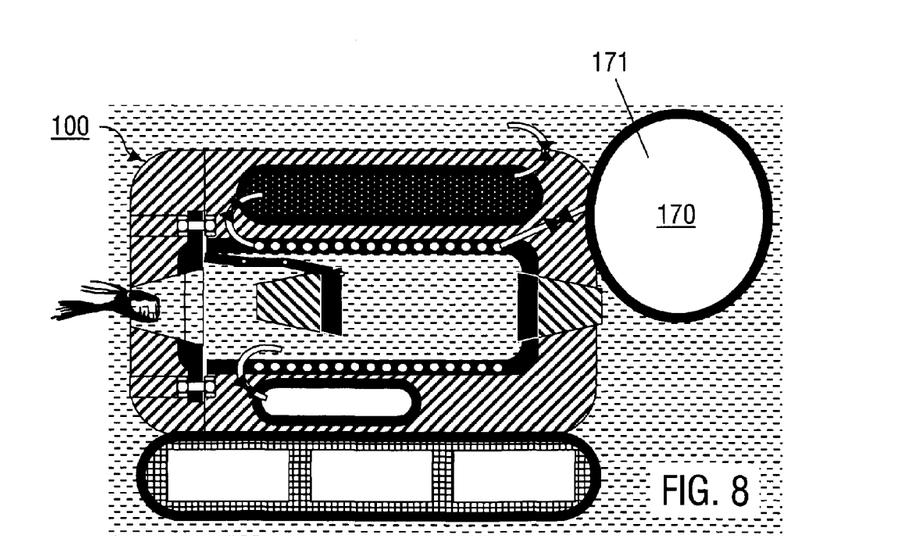

FIGS. 7 and 8 schematically illustrate a further embodiment of the conservation apparatus 100, which is equipped with a buoyancy device 170 and is otherwise of the same construction as the embodiment according to FIG. 5. The conservation apparatus 100 with the trapping device 110, the cooling device 120, the preparation device 140, the control device 150 and the buoyancy device 170 is shown in FIG. 7 in a state with an opened lid 115.1 shortly before the deep-sea fish 1 is collected. In this state, the coolant 3 is still in the coolant tank 121, valves 122.1 and 126.1 being closed. The outlet line 126 is connected to the buoyancy device 170.

The buoyancy device 170 comprises a buoyancy vessel 171, which is arranged on the outside of the internal wall 112 or (as shown) on the outside of the outer wall 114 such that, on pressurization with an internal pressure, it may be expanded or unfolded outwards. The buoyancy vessel 171 comprises for example a balloon made from a resilient material which is in particular elastically deformable at low temperatures, for example silicone or rubber, or a folded article made from sheets of metal or plastic (bellows). In FIG. 7, the collapsed state of the buoyancy device 170 before the start of cooling is shown schematically as an oval disc while FIG. 8 shows the expanded or unfolded state of the buoyancy device 170 which is formed during cooling.

In the conservation method according to the invention, before the start of cooling the external hydrostatic pressure initially compresses the buoyancy device 170 (FIG. 7). After the start of cooling, in particular after the valves 122.1, 126.1 have been opened, the cooling medium passes through the cooling line 125 and the outlet line 126 into the interior of the buoyancy device 170. Due to the heat exchange in the internal wall 112 or at the latest on emergence into the buoyancy device 170, the cooling medium is gaseous, such that the buoyancy device 170 is expanded or unfolded. The inventors have established that, even at the elevated hydrostatic pressure in the deep sea, a sufficiently elevated pressure is achieved to unfold the buoyancy device 170. The externally displaced volume of seawater provides buoyancy which causes the conservation apparatus 100 to surface.

Figure 9:
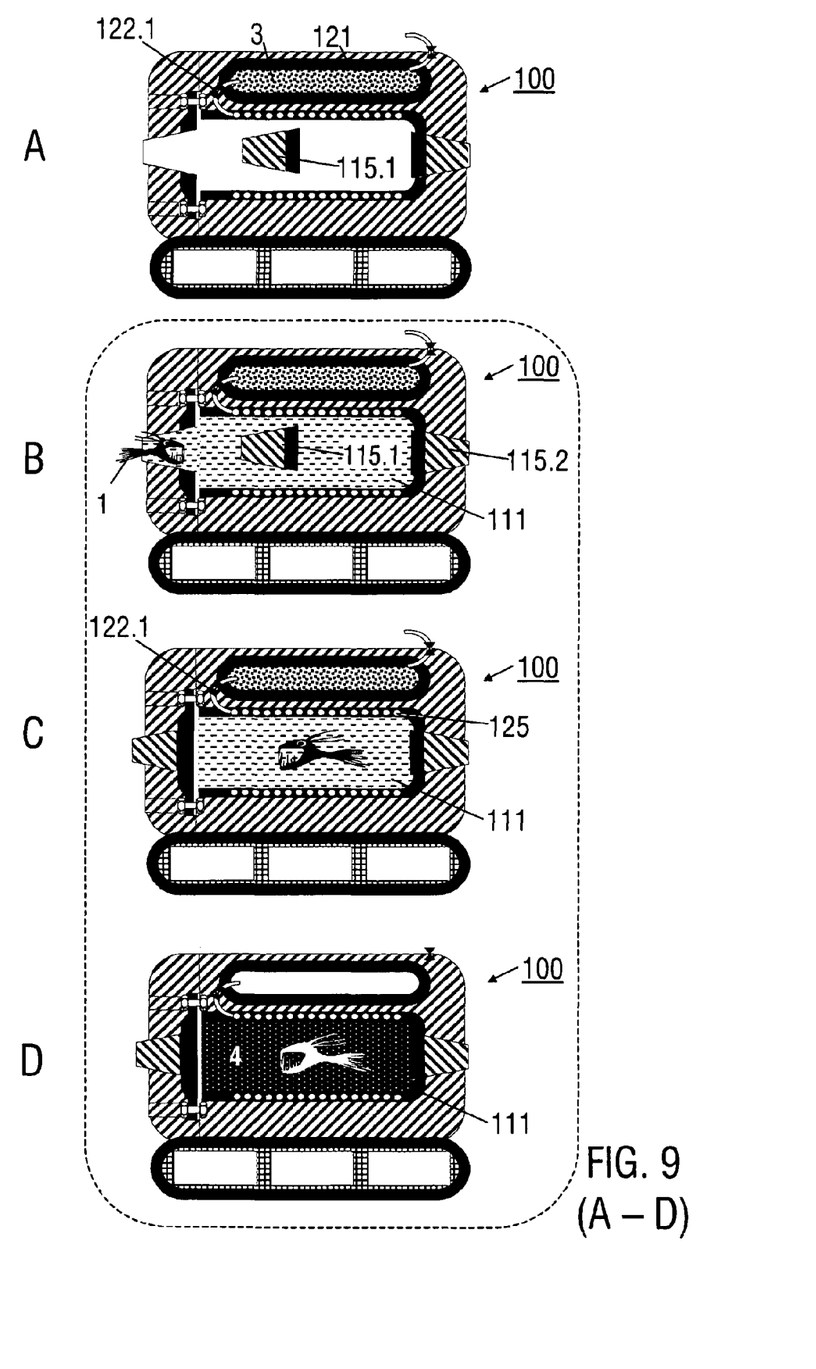

FIGS. 9A to 9G illustrate further details of the conservation method according to the invention. The dashed frame around FIGS. 9B to 9D indicates the method steps carried out in the deep sea or under elevated hydrostatic pressure. FIG. 9A shows the conservation apparatus 100 before immersion in the ocean. In this state, the lid 115.1 is open. The coolant tank 121 is filled with the coolant 3, for example liquid nitrogen. The valve in the feed line 122 is closed.

FIG. 9B shows the state of the conservation apparatus 100 in the deep sea, for example at a depth of 6000 m. With the lid 115.1 still open, the deep-sea fish 1 is lured into the chamber 111, for example by a messenger substance, a light source or a bait. Alternatively, both lids 115.1, 115.2 may be open and the deep-sea fish 1 may be flushed into the chamber 111.

When collecting of the deep-sea fish 1 in the chamber 111 is detected, the chamber 111 is closed (FIG. 9C). In this state, the cryoprotectant (see FIG. 5) may be introduced into the chamber 111. Cooling is then switched on. The feed valve 122.1 is opened, so that the cooling medium passes into the cooling line 125. The interior of the chamber 111 is cooled until ice forms, yielding a frozen solid 4 (FIG. 9D). In the state shown in FIG. 9D, the conservation apparatus 100 rises to the surface of the ocean, for example onto a ship and from there to a laboratory. The interior of the chamber 111 may be transferred as a solid 4 to the surface, independently of pressure and cryoconserved. While, on the basis of our current state of knowledge, the frozen deep-sea fish 1 is not completely conserved, it does contain cells which, having been cryoconserved, remain in a viable state and may be cultured in the following method steps (see below, FIG. 11). Because the deep-sea fish 1 is converted according to the invention into the frozen state, there is advantageously no time pressure during transport and the further steps in the surroundings under normal pressure.

At the surface, the trapping device 110 of the conservation apparatus 100 may be opened in cold surroundings. Part of the outer wall 114 and the front wall of the chamber 111 are removed for this purpose (FIG. 9E). Using a tool, for example a punch 129, the frozen solid 4 may be pushed out of the chamber 111 (FIG. 9F), in order to form an isolated frozen sample 5 consisting of the seawater and at least one biological organism (FIG. 9G).

Figure 10:
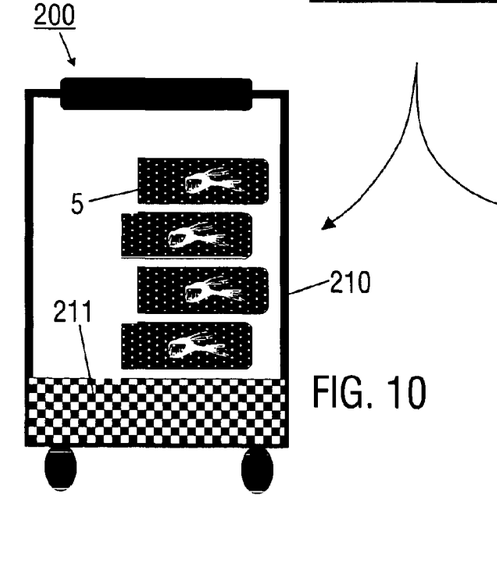
FIG. 10: shows a schematic illustration of the cryoconservation optionally provided under normal pressure.
Figure 11:
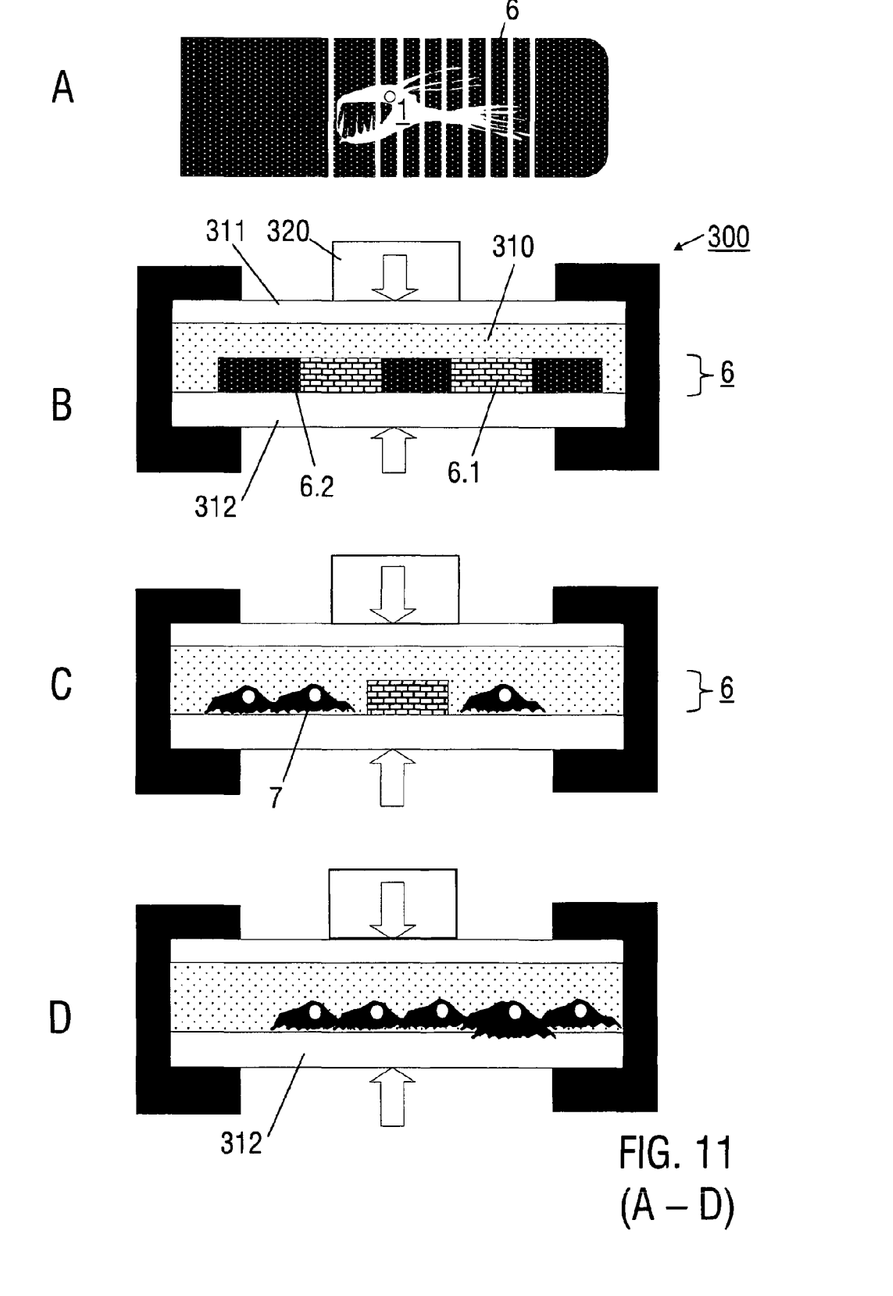

As the method proceeds, various options are available which are illustrated schematically in FIGS. 10 and 11. According to FIG. 10, the frozen sample 5 may be deposited in a cryoconservation device 200. The cryoconservation device 200 comprises for example a per se known cryotank 210 with a liquid coolant 211, for example liquid nitrogen, in the vapor from which the frozen sample 5 is stored. The cryoconservation of biological specimens is known per se, for which reason no further details are described here.

Immediately after the sample 5 (FIG. 9G) is obtained or after cryoconservation (FIG. 10), the sample 5 may be broken up and cells from the sample 5 cultured, as shown schematically in FIGS. 11A to 11D. According to FIG. 11A, the sample 5 is divided into sample sections 5. Each sample section 6 comprises a disc of the frozen solid with a thickness of for example 10 μm to 10 mm which contains frozen seawater and a tissue segment of the deep-sea fish 1. The sample 5 is broken up at temperatures below freezing point, in particular at a temperature in the range from −30° C. to −140° C. No cellular changes occur in this temperature range. While pressure relief may indeed result in recrystallization in the solid, this does not however, in particular if the organism is penetrated with a cryoprotectant, have an impact on the viability of the frozen cells. Any disadvantageous effects of recrystallization are mitigated by the addition of cryoprotectant prior to freezing.

A sample section 6, consisting of cells 6.1 and seawater 6.2, is then introduced into a culturing apparatus 300 (FIG. 11B). The culturing apparatus 300 comprises a chamber 310 with a layer-like, substantially two-dimensional internal volume, in which the sample section 6 is arranged. The culture chamber 310 is delimited by top and bottom plates 311, 312. Using a piezoelectric pressure generator 320, a pressure of up to 100 MPa may be produced in the interior of the culture chamber 310. In this state, cooling of the sample section 6 may be terminated. The temperature rises above the freezing point of the sample section 6, such that it thaws and releases cells 7 (shown magnified, FIG. 11C). As the method proceeds, the cells 7 may be cultured in the adherent state on the bottom plate 312 (FIG. 11D). To this end, the bottom plate 312 may be coated on its inner side, as is known per se from conventional cell culturing at normal pressure. A laminin or fibronectin coating is, for example, provided. As the method proceeds, the cells from the culture chamber 310 may be transferred into further culture chambers with optionally modified culture media in order to form a stable cell culture. For biological organisms having elevated pressure tolerance, culturing may proceed under lower pressure, for example at normal pressure.

The invention offers the following advantages. The conservation apparatus constitutes a freezing device for deep-sea use which may be constructed very largely without pressure stabilization. Any compressible gas volumes in the conservation apparatus are minimized. The conservation apparatus constitutes an extensively or completely pressure-independent system. Cryoconservation in the deep sea advantageously ensures the pressure tolerance of viable cells. Further advantages arise from the avoidance of the time pressure which occurs in conventional techniques for handling deep-sea organisms and from the preparation of the cells of the organisms in the deep-frozen state. It is advantageous that cells from organisms captured according to the invention may be converted, in particular by breaking up the organism, into a state readily culturable under pressure without loss of viability.

The features of the invention disclosed in the previous description, the drawings and the claims can be significant individually as well as in combination for the realization of the invention in its different embodiments.

The invention claimed is:

1. A method for conserving at least one biological organism in the deep sea, comprising the steps:
   collecting the biological organism with a trapping device in the deep sea,
   cooling the biological organism with a cooling device, wherein the biological organism is converted into a frozen state so as to provide a frozen biological organism, and
   moving the frozen biological organism into surroundings under normal pressure.

2. The method according to claim 1, in which the biological organism is frozen together with seawater in a chamber of the trapping device.

3. The method according to claim 1, in which the step of collecting the biological organism comprises:
   at least one of luring and actively flushing the biological organism into the trapping device.

4. The method according to claim 1, in which the cooling step comprises at least one of:
   introducing a fluid cooling medium into a hollow internal wall of the trapping device, and
   forming a thermal contact via at least one thermal bridge between a cooling medium and the internal wall of the trapping device.

5. The method according to claim 4, in which the introducing step comprises:
   displacing a fluid filling medium from the hollow internal wall of the trapping device.

6. The method according to claim 4, in which
   cooling is switched on at a predetermined start of cooling.

7. The method according to claim 6, in which:
   cooling is switched on as a function of a signal from a sensor device.

8. The method according to claim 1, in which
   the trapping device is moved by buoyancy in the sea, which is effected by conversion of a cooling medium into a gaseous state.

9. The method according to claim 1, further comprising the steps:
   detecting the biological organism in the trapping device, and
   adding a cryoprotectant to the trapping device.

10. The method according to claim 1, in which
    cooling is maintained in the surroundings under normal pressure.

11. The method according to claim 1 further comprising at least one of the steps of:
    breaking up the biological organism in the frozen state under normal pressure, and
    thawing the biological organism or parts of the biological organism under normal pressure or under elevated pressure.

12. The method according to claim 11, further comprising the step:
    culturing the biological organism or parts of the biological organism under normal pressure or under elevated pressure.

13. The method according to claim 1, in which:
    the step of moving the frozen biological organism into the surroundings under normal pressure comprises moving the trapping device with the frozen biological organism into the surroundings under normal pressure.

* * * * *